(12) United States Patent
McFadzean et al.

(10) Patent No.: US 10,721,506 B2
(45) Date of Patent: Jul. 21, 2020

(54) METHOD FOR CATALOGUING AND ACCESSING DIGITAL CINEMA FRAME CONTENT

(75) Inventors: David Bruce McFadzean, Canmore (CA); Monroe Milas Thomas, Calgary (CA)

(73) Assignee: CALGARY SCIENTIFIC INC., Calgary (CA)

( * ) Notice: Subject to any disclaimer, the term of this patent is extended or adjusted under 35 U.S.C. 154(b) by 629 days.

(21) Appl. No.: 13/533,071

(22) Filed: Jun. 26, 2012

(65) Prior Publication Data

US 2013/0007185 A1 Jan. 3, 2013

Related U.S. Application Data

(60) Provisional application No. 61/502,803, filed on Jun. 29, 2011.

(51) Int. Cl.
*G06F 15/16* (2006.01)
*H04N 21/239* (2011.01)
*H04N 21/81* (2011.01)
*H04N 21/4402* (2011.01)
*H04N 21/8352* (2011.01)
*H04N 21/414* (2011.01)

(52) U.S. Cl.
CPC ... *H04N 21/2393* (2013.01); *H04N 21/41407* (2013.01); *H04N 21/440236* (2013.01); *H04N 21/8153* (2013.01); *H04N 21/8352* (2013.01)

(58) Field of Classification Search
CPC ............ H04N 21/4307; H04N 21/8153; G06F 19/321; H04W 56/00; H04B 7/2693
USPC ........................................................ 709/231
See application file for complete search history.

(56) References Cited

U.S. PATENT DOCUMENTS 5,025,400 A    6/1991  Cook et al.
5,187,574 A    2/1993  Kosemura et al.
(Continued)

FOREIGN PATENT DOCUMENTS

CA    2261069    11/1998
CA    2239994    12/1998
(Continued)

OTHER PUBLICATIONS

Adalsteinsson, D., et al., "A Fast Level Set Method for Propagating Interfaces," Journal of Computational Physics, vol. 8, No. 2, Sep. 1994, pp. 269-277.

(Continued)

*Primary Examiner* — Kevin T Bates
*Assistant Examiner* — Clarence D McCray
(74) *Attorney, Agent, or Firm* — Meunier Carlin & Curfman LLC

(57) ABSTRACT

Systems and methods for providing remote access to a cinematic production. A server may generate and cache frames for a cinematic production while creating frame descriptors that are placed in the catalogue. A synchronization process synchronizes the catalogue with one or more clients. Using the catalogue, the client is able to select desired frames for viewing before frames are received at the client from the server. The server may receive a request for frames from the client, where the request includes an identifier component of the frame descriptor in the catalogue. The requested frames are returned by the server to the client for display at the client.

20 Claims, 5 Drawing Sheets

(56) References Cited

U.S. PATENT DOCUMENTS

| | | | |
|---|---|---|---|
| 5,886,733 A * | 3/1999 | Zdepski | H04N 7/173 348/423.1 |
| 6,028,608 A | 2/2000 | Jenkins | |
| 6,119,154 A * | 9/2000 | Weaver | H04N 21/2387 348/E5.008 |
| 6,271,847 B1 | 8/2001 | Shum et al. | |
| 6,674,430 B1 | 1/2004 | Kaufman et al. | |
| 6,888,551 B2 | 5/2005 | Willis et al. | |
| 7,333,236 B2 | 2/2008 | Herrmann | |
| 7,370,120 B2 | 5/2008 | Kirsch et al. | |
| 7,379,605 B1 * | 5/2008 | Ticsa | G06F 19/321 382/232 |
| 7,430,261 B2 * | 9/2008 | Forest et al. | 375/364 |
| 7,432,935 B2 | 10/2008 | Keller | |
| 7,519,209 B2 | 4/2009 | Dawant et al. | |
| 7,526,131 B2 | 4/2009 | Weber | |
| 7,574,247 B2 | 8/2009 | Moreau-Gobard et al. | |
| 7,586,953 B2 * | 9/2009 | Forest | H03M 13/43 370/230 |
| 7,606,314 B2 | 10/2009 | Coleman et al. | |
| 7,647,331 B2 | 1/2010 | Li et al. | |
| 7,912,259 B2 | 3/2011 | Arditi et al. | |
| 8,005,369 B2 * | 8/2011 | Ko et al. | 398/154 |
| 8,265,449 B2 * | 9/2012 | Nagahara et al. | 386/224 |
| 8,503,754 B2 | 8/2013 | Roberts et al. | |
| 8,589,995 B2 * | 11/2013 | Choi et al. | 725/113 |
| 8,620,861 B1 * | 12/2013 | Uhrhane | G06F 16/1873 707/610 |
| 2002/0101429 A1 | 8/2002 | Abdo | |
| 2003/0025599 A1 | 2/2003 | Monroe | |
| 2003/0081840 A1 | 5/2003 | Palmer et al. | |
| 2004/0005005 A1 | 1/2004 | McIntyre et al. | |
| 2005/0033758 A1 * | 2/2005 | Baxter | 707/100 |
| 2005/0100220 A1 | 5/2005 | Keaton et al. | |
| 2005/0105786 A1 | 5/2005 | Moreau-Gobard et al. | |
| 2005/0110791 A1 | 5/2005 | Krishnamoorthy et al. | |
| 2005/0111718 A1 | 5/2005 | MacMahon et al. | |
| 2006/0008254 A1 * | 1/2006 | Seo | 386/120 |
| 2006/0013482 A1 | 1/2006 | Dawant et al. | |
| 2006/0173272 A1 | 8/2006 | Qing et al. | |
| 2006/0222081 A1 | 10/2006 | Carrigan | |
| 2007/0031019 A1 | 2/2007 | Lesage et al. | |
| 2007/0036402 A1 | 2/2007 | Cahill et al. | |
| 2007/0103567 A1 | 5/2007 | Wloka | |
| 2007/0162568 A1 * | 7/2007 | Gupta | G06Q 30/0242 709/219 |
| 2008/0008401 A1 | 1/2008 | Zhu | |
| 2008/0126487 A1 * | 5/2008 | Wegenkittl | G06F 19/321 709/205 |
| 2008/0137921 A1 | 6/2008 | Simon et al. | |
| 2008/0143718 A1 | 6/2008 | Ray et al. | |
| 2008/0175377 A1 * | 7/2008 | Merrill | 380/30 |
| 2008/0246770 A1 | 10/2008 | Kiefer et al. | |
| 2009/0083809 A1 * | 3/2009 | Hayashi | H04N 5/783 725/88 |
| 2009/0087161 A1 | 4/2009 | Roberts et al. | |
| 2009/0125570 A1 * | 5/2009 | Bailey | G06F 17/30244 |
| 2009/0150557 A1 * | 6/2009 | Wormley | H04N 21/23424 709/231 |
| 2010/0229201 A1 * | 9/2010 | Choi et al. | 725/54 |
| 2011/0085025 A1 * | 4/2011 | Pace | H04N 9/8205 348/49 |
| 2011/0126127 A1 * | 5/2011 | Mariotti | G06F 19/321 715/753 |
| 2011/0202947 A1 * | 8/2011 | Gupta et al. | 725/14 |
| 2011/0202966 A1 * | 8/2011 | Gupta et al. | 725/114 |
| 2011/0310446 A1 * | 12/2011 | Komatsu | H04N 1/6011 358/518 |
| 2012/0011568 A1 * | 1/2012 | Tahan | G06F 3/0481 726/4 |
| 2012/0084350 A1 * | 4/2012 | Xie | G06F 9/5088 709/203 |
| 2012/0200774 A1 * | 8/2012 | Ehlers, Sr. | 348/515 |
| 2012/0310660 A1 * | 12/2012 | Liu | G06F 19/3418 705/2 |
| 2013/0019257 A1 * | 1/2013 | Tschernutter | H04N 21/234309 725/4 |
| 2013/0163835 A1 * | 6/2013 | Park | G06F 19/321 382/128 |
| 2013/0179186 A1 * | 7/2013 | Birtwhistle | G06F 17/30578 705/3 |
| 2013/0215246 A1 * | 8/2013 | Ozaki | A61B 1/00057 348/77 |
| 2013/0227013 A1 * | 8/2013 | Maskatia | H04L 65/403 709/204 |
| 2015/0046953 A1 * | 2/2015 | Davidson | G06K 9/00758 725/74 |
| 2015/0163379 A1 * | 6/2015 | Herzog | H04N 21/8547 348/500 |

FOREIGN PATENT DOCUMENTS

| | | |
|---|---|---|
| CA | 2427590 | 5/2001 |
| EP | 1744287 | 4/2008 |
| WO | 2010/085898 | 8/2010 |
| WO | 2010/085899 | 8/2010 |

OTHER PUBLICATIONS

Baillard, C., et al., "Robust Adaptive Segmentation of 3D Medical Images with Level Sets," INRIA, Rennes, France, Research Report No. 1369, Nov. 2000, 28 pages.

Billeter, M., et al., "Efficient Stream Compaction on Wide SIMD Many-Core Architectures," Proceedings of the ACM SIGGRAPH/EUROGRAPHICS Conference on High Performance Graphics, HPG, 2009, pp. 159-166.

Boulos, S., et al., "Interactive Distribution Ray Tracing," Technical report UUSCI-2006-022, SCI Institute, University of Utah, 2006, 13 pages.

Bülow, T., "A General Framework for Tree Segmentation and Reconstruction from Medical Volume Data," Proceedings of the 7$^{th}$ International Conference on Medical Image Computing and Computer-Assisted Intervention, Saint-Malo, France, MICCAI, vol. 3216, 2004, pp. 533-540.

Carrillo, J., et al., "Recursive tracking of vascular tree axes in 3D medical images," International Journal of Computer Assisted Radiology and Surgery, vol. 1, Issue 6, Apr. 2007, pp. 331-339.

Cates, J.E., et al., "GIST: an interactive, GPU-based level set segmentation tool for 3D medical images," Medical Image Analysis, vol. 8, Issue 3, 2004, pp. 217-231.

Christensen, P.H., et al., "Ray Differentials and Multiresolution Geometry Caching for Distribution Ray Tracing in Complex Scenes," Computer Graphics Forum (Eurographics 2003 Conference Proceedings), 2003, pp. 543-552.

Cocosco, C.A., et al., "BrainWeb: Online Interface to a 3D MRI Simulated Brain Database," NeuroImage, vol. 5, No. 4, 1997, p. 425.

Deschamps, T., "Curve and Shape Extraction with Minimal Paths and Level-Sets Techniques. Applications to 3D Medical Imaging," Ph.D. thesis, Université Paris-IX, Dauphine, 2001, 233 pages.

Kindlmann, G., et al., "Curvature-based transfer functions for direct volume rendering: methods and applications," Proceedings of the 14$^{th}$ IEEE Visualization, 2003, pp. 513-520.

Lefohn, A.E., et al., "A Streaming Narrow-Band Algorithm: Interactive Computation and Visualization of Level Sets," IEEE Transactions on Visualization an dComputer Graphics, vol. 10, No. 4, 2004, pp. 422-433.

Lefohn, A.E., et al., "Interactive Deformation and Visualization of Level Set Surfaces Using Graphics Hardware," IEEE Visualization, 2003, pp. 75-82.

Lefohn, A.E., et al., "Interactive, GPU-Based Level Sets for 3D Brain Tumor Segmentation," Apr. 16, 2003, 15 pages.

Lefohn, A.E., et al., Interactive, GPU-Based Level Sets for 3D Segmentation, MICCAI, 2003, pp. 564-572.

(56) References Cited

OTHER PUBLICATIONS

Månsson, E., et al., "Deep Coherent Ray Tracing," Proceedings of the 2007 IEEE Symposium on Interactive Ray Tracing, RT, IEEE Computer Society, 2007, pp. 79-85.
Peng, D., et al., "A PDE-Based Fast Local Level Set Method," Journal of Computational Physics, vol. 155, No. 2, 1999, pp. 410-438.
Rumpf, M., et al., "Level set segmentation in graphics hardware," Proceedings of IEEE International Conference on Image Processing, ICIP, vol. 3, 2001, pp. 1103-1106.
Schmittler, J., et al., "SaarCOR—A Hardware Architecture for Ray Tracing," Graphics Hardware, 2002, 11 pages.
Sengupta, S., et al., "Scan Primitives for GPU Computing," Graphics Hardware, 2007, 11 pages.
Sherbondy, A., et al., "Fast Volume Segmentation With Simultaneously Visualization Using Programmable Graphics Hardware," Proceedings of the $14^{th}$ IEEE Visualization 2003, VIS, 2003, pp. 171-176.
Taheri, S. "3D Tumor Segmentation using Level Set," Course Notes, National University of Singapore, Apr. 2006, 40 pages.
Taheri, S., "Level-set segmentation of brain tumors in magnetic resonance images," Ph.D. thesis, National University of Singapore, Jul. 2007, 155 pages.
Whitaker, R.T., "A Level-Set Approach to 3D Reconstruction from Range Data," International Journal of Computer Vision, vol. 29, No. 3, 1998, pp. 203-231.
Zhou, T., et al., "Accurate depth of field simulation in real time," Computer Graphics Forum, vol. 26, 2007, pp. 15-23.
Extended European Search Report, dated Mar. 4, 2013, received in connection with European Application No. 10735473.0.
International Search Report and Written Opinion, dated Nov. 9, 2012, received in connection with International Application No. PCT/IB2012/001273.
International Search Report, dated Apr. 26, 2010, received in connection with International Application No. PCT/CA2010/000152.
International Preliminary Report on Patentability and Written Opinion, dated Aug. 2, 2011, received in connection with International Application No. PCT/CA2010/000152.
International Search Report, dated May 19, 2010, received in connection with International Application No. PCT/CA2010/000153.
International Preliminary Report on Patentability and Written Opinion, dated Aug. 2, 2011, received in connection with International Application No. PCT/CA2010/000153.
Roberts, Mike, et al., "A work-efficient GPU algorithm for level set segmentation," in Proceedings of the Conference on High Performance Graphics (HPG '10, Eurographics Association, Aire-la-Ville, Switzerland, 2010, pp. 123-132.
Ledergerber, C., et al., "Volume MLS Ray Casting," IEEE Transactions on Visualization and Computer Graphics, vol. 14, No. 6, 2008, pp. 1372-1379.

* cited by examiner

METHOD FOR CATALOGUING AND ACCESSING DIGITAL CINEMA FRAME CONTENT

CROSS-REFERENCE TO RELATED APPLICATION

The present application claims priority to U.S. Provisional Patent Application No. 61/502,803, filed Jun. 29, 2011, and entitled "Method for Cataloguing and Accessing Digital Cinema Frame Content," which is incorporated herein by reference it is entirety.

BACKGROUND

Ubiquitous remote access to application programs and data has become commonplace as a result of the growth and availability of broadband and wireless network access. In addition, users are accessing application programs and data using an ever-growing variety of client devices (e.g., mobile devices, table computing devices, laptop/notebook/desktop computers, etc.). Data may be communicated to the mobile device from a remote server over a 3G and 4G mobile data networks or wireless networks such as WiFi and WiMax. Most mobile devices have access to the Internet and are able to interact with various types of application programs.

However, with respect to certain classes of devices (e.g., mobile devices accessing data over slower networks) remote access to cinematic productions is somewhat problematic in high latency settings, such as in mobile data networks or where there is a requirement for high bandwidth. Cinematic productions are a sequence of images that are pre-assembled into an animation, as opposed to video streaming. In addition, because the mobile devices have no knowledge of data until it is received, an end user typically must wait for image data to be provided before a request to view the imagery can be made. In other environments, quick sampling of the image data may lead to missed frames. In yet other environments, if a server is producing frames quicker than the client can consume them, the client may not be able to show all of the frames. While this may be desirable in order to keep up with the server, there are other situations where such a mode of operation is not acceptable, such as in radiology, where a clinician may miss a frame with abnormal pathology, resulting in misdiagnosis. In other environments, if the server is generating frames in an on-demand fashion, every time a frame is requested by a client it has to be generated or re-generated, thus consuming server resources.

SUMMARY

Disclosed herein are systems and methods for remotely accessing a cinematic production. In accordance with some implementations, there is provided a method of providing remote access to a cinematic production. The method may include generating a frame from the cinematic production at a server, generating a frame descriptor associated with the frame at the server, storing the frame in a first memory, storing the frame descriptor in a catalogue in a second memory, and synchronizing the catalogue with a remote client. The frame descriptor may be provided for requesting the frame.

In accordance with some implementations, there is provided another method for remotely accessing a cinematic production. The method may include receiving a catalogue of frame descriptors from a server, requesting a frame of the cinematic production from the server using at least one frame identifier from the catalogue as a request, receiving the frame from the server, and caching the frame in a cache.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for remotely accessing and viewing cinematic productions, it will become evident to those skilled in the art that the implementations are not limited thereto, but are applicable for remotely accessing any audio, video or still imagery via a mobile device.

Figure 1:
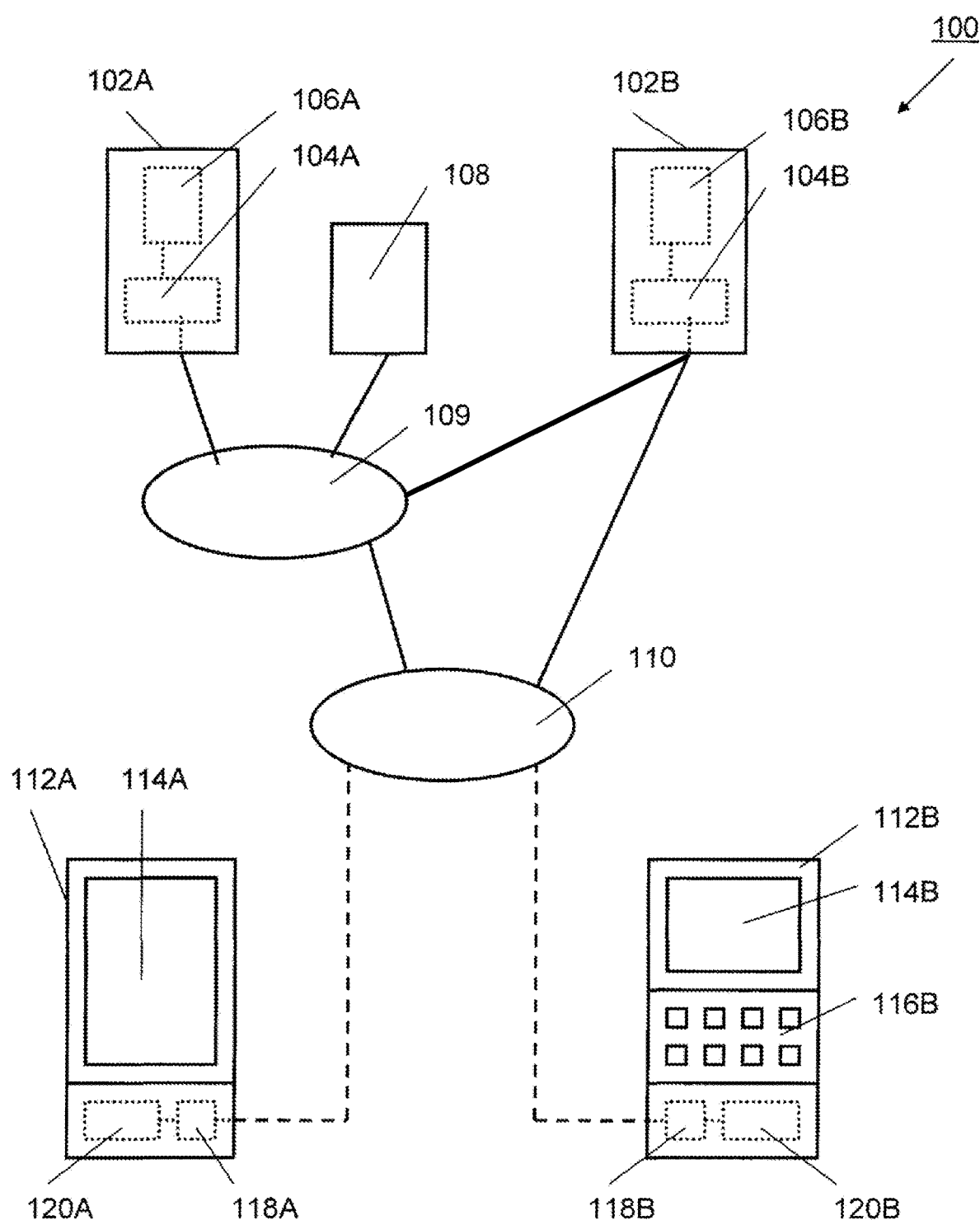
FIG. 1 is a simplified block diagram illustrating a system for providing remote access to a cinematic production from a mobile device via a computer network.

Referring to FIG. 1, a system 100 for providing remote access to a cinematic production via a computer network. The system comprises a client computer 112A or 112B, such as a wireless handheld device such as, for example, an IPHONE 112A or a BLACKBERRY 112B connected via a computer network 110 such as, for example, the Internet, to server computer 102B. The client computer may also be an IPAD or ANDROID-base computing device. The server computer 102B is connected, for example, via the computer network 110 to a Local Area Network (LAN) 109 or may be directly connected to the computer network 110. For example, the LAN 109 is an internal computer network of an institution such as a hospital, a bank, a large business, or a government department. Typically, such institutions still use a mainframe computer 102A and a database 108 connected to the LAN 109. Numerous application programs may be stored in memory 106A of the mainframe computer 102A and executed on a processor 104A. Similarly, numerous application programs may be stored in memory 106B of the server 102B and executed on a processor 104B. The mainframe computer 102A, the server 102B and the client computers 112A/112B may be implemented using hardware such as that shown in the general purpose computing device of FIG. 5. In accordance with aspects of the present disclosure, remote access to cinematic productions may be provided to, for example, a handheld wireless device (clients 112A/112B) by an application program executing on the processor 104B of the server computer 102B, as described with reference to FIG. 4.

A user interface program (not shown) may be designed for providing user interaction via a hand-held wireless device for displaying data and/or imagery in a human comprehensible fashion and for determining user input data in dependence upon received user instructions for interacting with the application program using, for example, a graphical display with touch-screen 114A or a graphical display 114B and a keyboard 116B of the handheld wireless device 112A, 112B, respectively. For example, the user interface program is performed by executing executable commands on processor 118A, 118B of the client computer 112A, 112B with the commands being stored in memory 120A, 120B of the client computer 112A, 112B, respectively.

Alternatively, the user interface program is executed on the server computer 102B which is then accessed via an URL by a generic client application such as, for example, a web browser executed on the client computer 112A, 112B. The user interface is implemented using, for example, Hyper Text Markup Language HTML 5.

The user interface program may provide a function to enter and exit a cinematic viewing mode. The user interface program may enable the user to forward reverse, pause and stop the viewing of the cinematic production. The user interface program may also display the actual frames per second (FPS), throttle the speed of the cinematic production, provide a looping feature, and provide an indicator to signal that caching/buffering of images of the cinematic production is complete.

Figure 2:
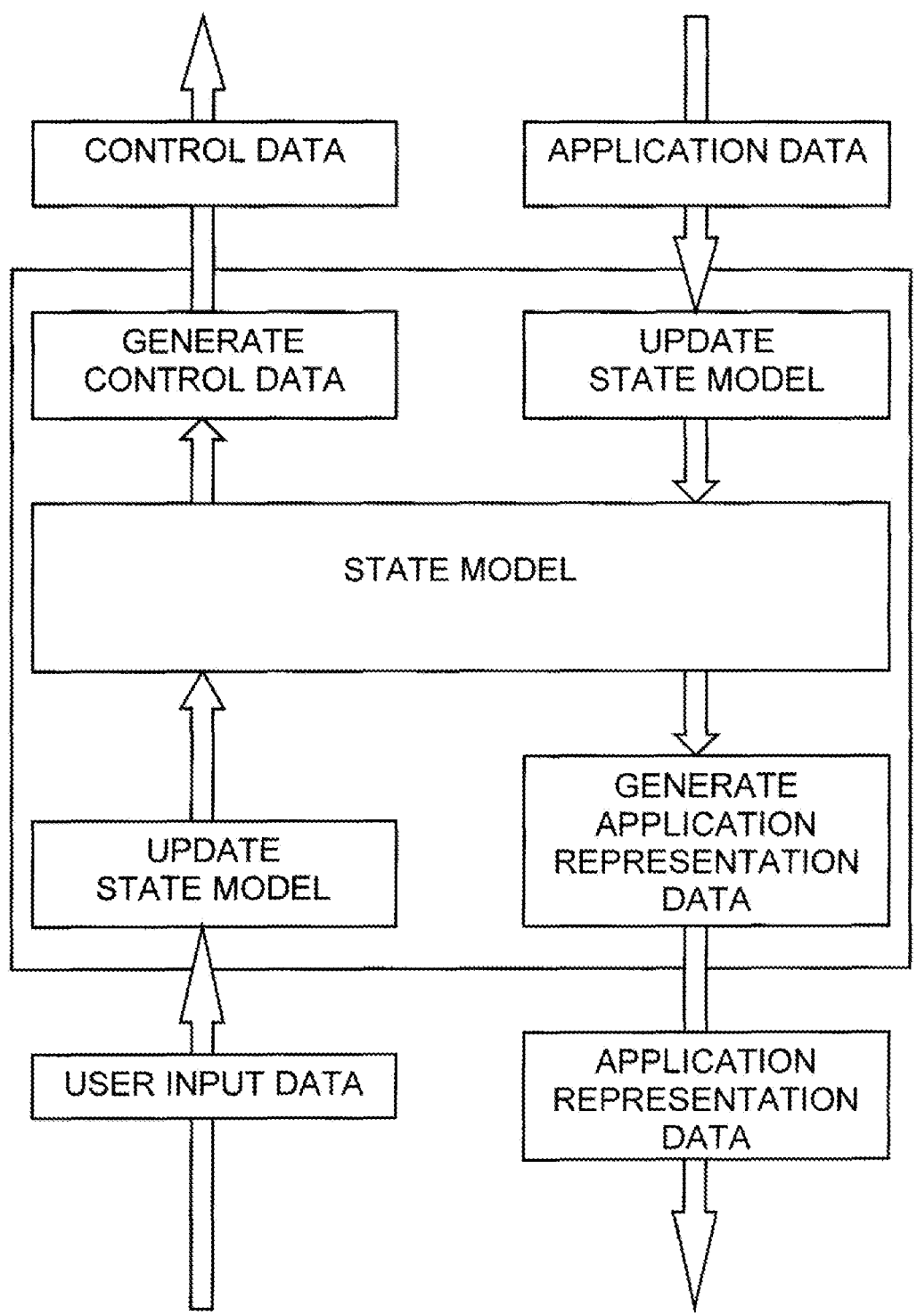
FIG. 2 is a simplified block diagram illustrating operation of the remote access program.

A remote access program may be executing on the client (see, FIG. 3) that determines control data in cooperation with user input data received from the user interface program and provides the same to server 102B. The remote access program may be executed using the processor 118A, 118B of the client computer 112A, 112B, respectively. Alternatively, the remote access program may be executing on the processor 104B of the server computer 102B and accessed by a URL through a LAN 109 connection via computer network 110, as illustrated in FIG. 1. The operation of the remote access program is performed in cooperation with a state model of the application program, as illustrated in FIG. 2. When executed, the remote access program updates the state model in dependence upon user input data received from a user interface program, generates control data in dependence upon the updated state model, and provides the same to the application program. Upon receipt of application data or the cinematic production, the remote access program updates the state model in dependence upon the application data received from the application program, generates application representation data in dependence upon the updated state model, and provides the same to the user interface program.

The state model comprises an association of logical elements of the application program with corresponding states of the application program with the logical elements being in a hierarchical order. The state model may be determined such that each of the logical elements is associated with a corresponding state of the application program. Further, the state model may be determined such that the logical elements are associated with user interactions. For example, the logical elements of the application program are determined such that the logical elements comprise transition elements with each transition element relating a change of the state model to one of control data and application representation data associated therewith.

Figure 3:
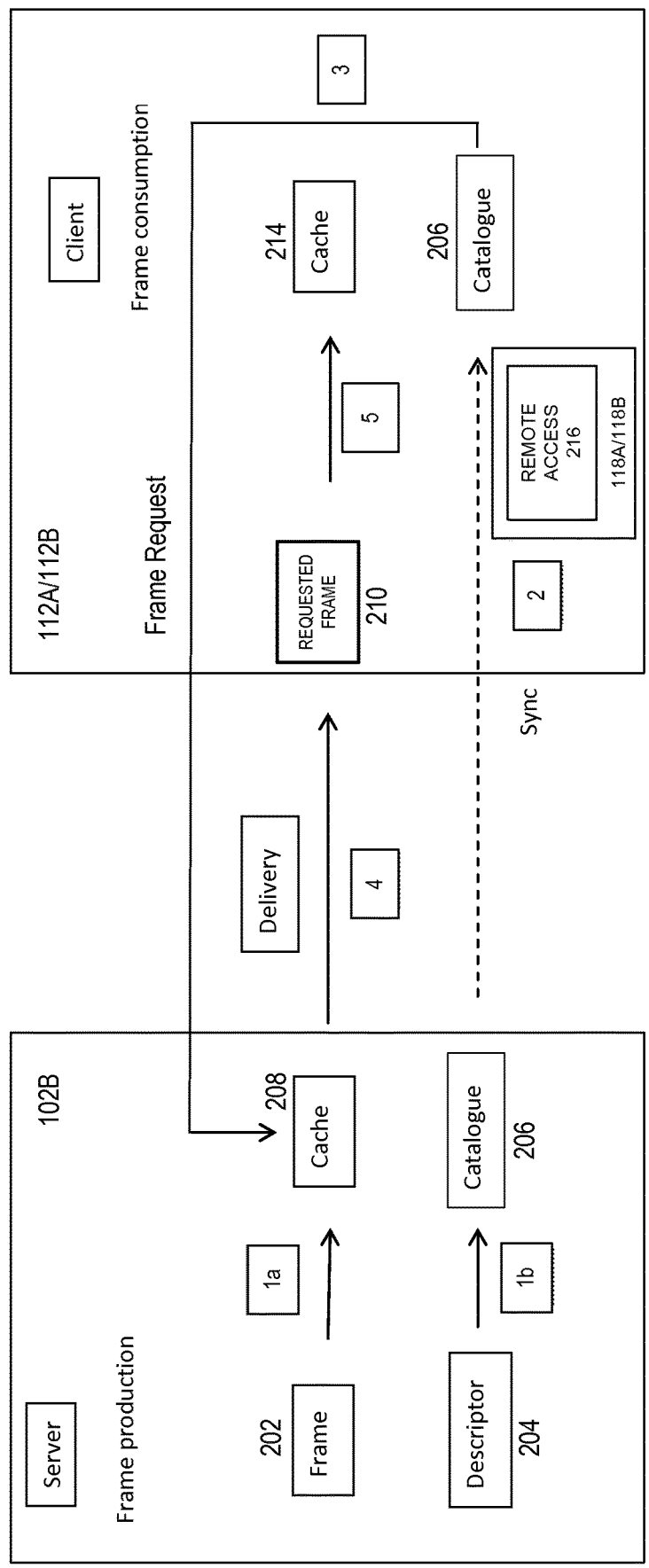
FIG. 3 illustrates the system of FIG. 1 in greater detail.

With reference to FIG. 3, there is shown the system of FIG. 1 in greater detail. As illustrated, implementations of the present disclosure may include the server 102B and client(s) 112A/112B. More than one server may be implemented, as well as any number of clients. The server 102B begins by generating frames 202 from a cinematic production and placing them into a cache 208. The generated frames 202 are retained in the cache 208, such that the server 102B does not need to regenerate frames 202 that have been previously generated. Each frame 202 may be one of many single images that comprise the cinematic production. A descriptor 204 of the frame is placed into a data structure (catalogue 206). The cache 208 and the catalogue 206 may be stored in a memory of the server, as described with reference to the general purpose computing device shown in FIG. 5. However, in accordance with implementations of the present disclosure, the frames 202 in the cache 208 and the associated frame descriptor 204 in the catalogue 206 are separately maintained (i.e., decoupled) in the memory of the server 102B. The memory may be any type of storage media, such as RAM, a hard disk, a solid state drive, optical media, etc.

The client 112A/112B may initiate the production of frames sending a request to the server 102B, or the server 102B may begin generating the frames autonomously. In generating the frames 202, the server 102B also generates the frame descriptor 204. For example, the frame descriptor 204 includes at least an identifier, such as random number or other association that is used to lookup the frame 202. The frame descriptor 204 may also be a combination of the identifier and associated metadata (e.g., a MRI slice number, a time, image dimensions, file format, author, etc.) provided by an application that created the cinematic production. For example, the MRI slice number may be generated by a scanning device. The catalogue 206, comprised of frame descriptors 204, may grow or be changed dynamically by the server 102B in accordance with the frames generated and/or removed or a combination of both.

The client 112A/112B may observe the catalogue 206 through a synchronization technique. For example, PUREWEB, available from Calgary Scientific, Inc. of Calgary, Alberta, may be used to synchronize the catalogue 206 between the server 102B and the client 112A/112B. Other communications techniques may be use for synchronization. The catalogue 206 may be partially synchronized between the server 102B and the client 112A/112B by transmitting only changes to the catalogue 206 (modifications, additions and/or deletions of frame descriptors) or fully synchronized by transmitting the entire catalogue 206. A combination of partial and full synchronizations may be used depending on a configuration setting. Thus, the client 112A/112B maintains a duplicate of catalogue that is stored on the server 102B. As will be described below, using the catalogue 206, a remote access program 216 executing on the processor 104A/104B of the client 112A/112B may select what frames to view, and how to view the frames (e.g., where to start viewing frames, whether to skip frames for faster speed, etc.). Using the state manager (See, FIG. 2), an application state of the server 102B can be synchronized with client 112A/112B as frames 202 are generated, such that the synchronization of the catalogue 206 can be a dynamic process with the client 112A/112B observing the catalogue 206 as it is changing at the server 102B.

In some implementations, the client 112A/112B may be provided with a local cache 214 to store one or more request frames 210 from the server. If the client already has a frame 202 in its cache, the client 112A/112B need not request the frame from the server 102B, but rather may retrieve it from the local cache 214 for display. This serves to reduce bandwidth requirements and lag time, thus increasing the perceived responsiveness of the client 112A/112B.

With the system illustrated in FIG. 3, the local cache 214 may hold, for example, approximately 100-200 images. The operation of the cache 214 as it relates to playback at the client device 112A/112B is as follows. If the cache is set to 200 frames; then let C=current frame being seen by the user and M=total number of frames (slices) in series. The notation '[' or ']' indicates inclusive and the notation '(' or ')' indicate exclusive. The first frame played will be "C" and the range of frames played is calculated as follows:

If M<=200, [0, M] is played.
else If C−100 is <0, [0−200) is played.
else If C+100 is >=M, [M−200, M] is played
else [C−100, C+100) is played.

In addition to the above, the size of the local cache 214 may be configurable. JPEG Images may be transmitted having a quality of between 85 and 100 to provide for memory management of the cache size.

Figure 4:
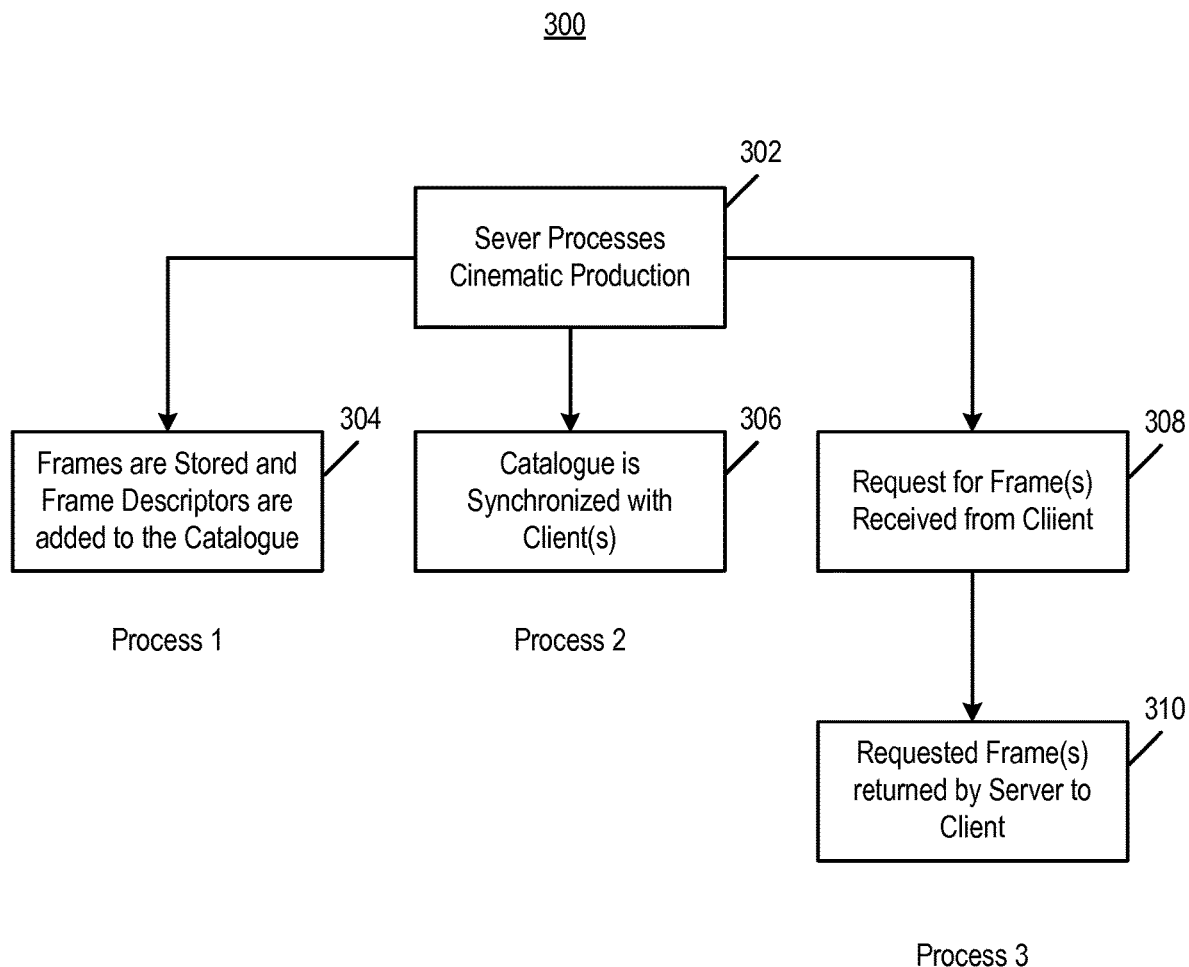
FIG. 4 illustrates a flow diagram of example operations performed within the system of FIGS. 1-3.

FIG. 4 illustrates a flow diagram 300 of example operations performed within the system of FIGS. 1-3. In general, the server 102B performs a cinematic production process 302 that may spawn three separate processes. A first process generates and caches frames, and creates the frame descriptors that are placed in the catalogue (304).

A second process is a synchronization process that synchronizes the catalogue with one or more clients (306). In accordance with aspects of the present disclosure, the catalogue 206 may be simultaneously synchronized with plural clients. Each of the clients receives the catalogue 206 and remains in synchronism with the server 102B and each other. From the catalogue 206, the client 112A/112B is able to select desired frames for viewing before frames are received at the client 112A/112B from the server 102B. In other words, the client 112A/112B knows in advance what is stored in the cache of the server 102B because of the information contained in the catalog 206.

A third process provides frame data to the client in response to a client request. The server may receive a request from the client (308). The client 112A/112B may request frames 202 using the identifier component of the frame descriptor in the catalogue 206. For example, the metadata of the frame descriptor 204 may be used on the client 112A/112B as search criteria, whereby an end user may run a search against the metadata to retrieve frames from the server 112A (or cache 214, as described below) that correspond to the search results. Because the metadata is linked to the identifier in the frame descriptor 204, the client 112A/112B is able to request the appropriate frame (or frames) using the identifier(s). In another example, the metadata may be a timestamp. In yet another example, the client 112A/112B may generate a globally unique identifier (GUID) that is passed to the server as an identifier. The client 112A/112B may request frames 202 using identifiers in the frame descriptors 204 associated with a range of timestamps of interest. The client 112A/112B may specify a maximum frame rate to limit the size of the frame cache 214. The frame rate may be between 15 and 30 FPS for images having a size of approximately 512×512 pixels. A higher frame rate of approximately 45 FPS may be achieved where smaller image sizes are communicated to the client 112A/112B. The client 112A/112B may also specify an encoding quality of the frames to be transferred, a destination path and/or a list of frames using GUIDs.

At 310, the requested frames are returned by the server to the client. The server 102B may add the frames to the cache 208 as raw RGB images and encoded in accordance with the client request. The GUID and metadata may be added to the frame catalogue 206 as the frames are added to the cache 208. The frames 202 may be transmitted by any communication technique to the client 112A/112B and stored in the cache 214. For example, a MIME type may be specified (e.g., image/x-tile, image/jpeg or image/png or other). Once the client 112A/112B buffers enough data, the client will begin playback of the images.

In some implementations, the client request may be in a message that contains at least one or more identifiers. The client may also send the metadata component of the frame descriptor in the message. The server responds by sending the requested frame(s) to the client in a message. The client unpacks the frames from the message and places the frames in the local cache. The frames may then be processed by the graphics subsystem of client and displayed to the end user.

In accordance with some implementations, the system 100 may buffer a minimum number of frames for playback on the client 112A/112B within approximately one minute. The playback of may begin within ten seconds of a user activating the cinematic viewing mode within the user interface program.

It is noted that processes of FIG. 4 of generating the frames and catalogue, synchronization of catalogue, and frame request(s)/serving may be performed simultaneously and asynchronously.

In some implementations, synchronization of the catalogue on plural clients may be used in a collaboration setting where different clients can independently choose different views. For example, if a client is connected to the server by a slow network connection, the client may skip frames, whereas a client connected by a faster network connection may receive all frames. However, each of the clients in the collaboration receives and interacts with the same cinematic production.

Figure 5:
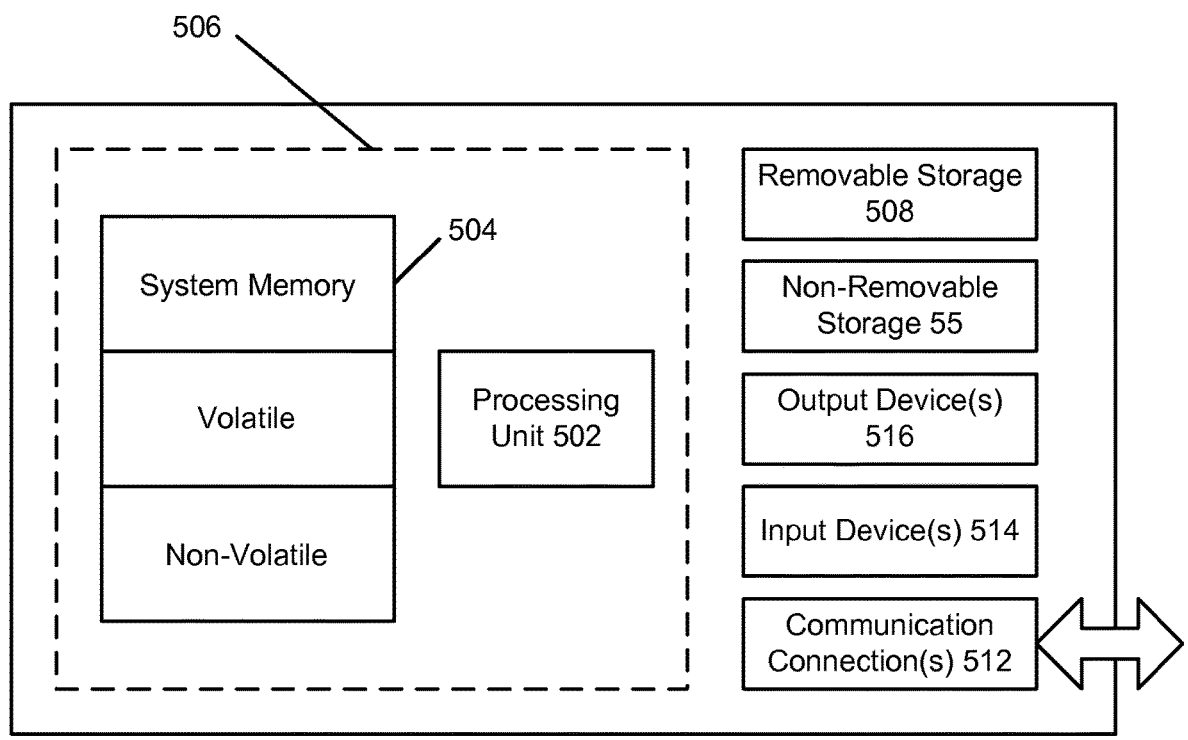
FIG. 5 shows an exemplary computing environment in which example embodiments and aspects may be implemented.

FIG. 5 shows an exemplary computing environment in which example embodiments and aspects may be implemented. The computing system environment is only one example of a suitable computing environment and is not intended to suggest any limitation as to the scope of use or functionality.

Numerous other general purpose or special purpose computing system environments or configurations may be used. Examples of well known computing systems, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 5, an exemplary system for implementing aspects described herein includes a computing device, such as computing device 500. In its most basic configuration, computing device 500 typically includes at least one processing unit 502 and memory 504. Depending on the exact configuration and type of computing device, memory 504 may be volatile (such as random access memory (RAM)), non-volatile (such as read-only memory (ROM), flash memory, etc.), or some combination of the two. This most basic configuration is illustrated in FIG. 5 by dashed line 506.

Computing device 500 may have additional features/functionality. For example, computing device 500 may include additional storage (removable and/or non-removable) including, but not limited to, magnetic or optical disks or tape. Such additional storage is illustrated in FIG. 5 by removable storage 508 and non-removable storage 510.

Computing device 500 typically includes a variety of computer readable media. Computer readable media can be any available media that can be accessed by device 500 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 504, removable storage 508, and non-removable storage 510 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 500. Any such computer storage media may be part of computing device 500.

Computing device 500 may contain communications connection(s) 512 that allow the device to communicate with other devices. Computing device 500 may also have input device(s) 514 such as a keyboard, mouse, pen, voice input device, touch input device, etc. Output device(s) 516 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method of providing remote access to a cinematic production, comprising:
   generating a frame from the cinematic production at a server;
   generating a frame descriptor associated with the frame at the server;
   storing the frame in a first memory;
   storing the frame descriptor in a catalogue of frame descriptors in a second memory of the server; and
   synchronizing the catalogue with a duplicate of the catalogue of frame descriptors maintained a remote client such that the duplicate of the catalogue of frame descriptors maintained at the remote client is updated to reflect dynamic changes in the catalogue of frame descriptors in the second memory of the server,
   wherein the frame descriptor in the duplicate of the catalogue of frame descriptors maintained at the client is for providing a request for the frame from the remote client.

2. The method of claim 1, further comprising storing the frame in a cache.

3. The method of claim 1, further comprising:
   receiving a request from the remote client for the frame;
   retrieving the frame; and
   communicating the frame to the remote client.

4. The method of claim 3, further comprising generating the frame in response to the request from the remote client.

5. The method of claim 3, wherein the request includes a unique identifier of the frame that is provided with the frame descriptor.

6. The method of claim 5, wherein the unique identifier is a globally unique identifier that is provided by the remote client.

7. The method of claim 3, further comprising:
   receiving plural requests for frames of the cinematic production from plural clients that are viewing the frames of the cinematic production in a collaborative environment.

8. The method of claim 7, wherein the plural requests are for different views of the cinematic production.

9. The method of claim 1, further comprising dynamically updating the catalogue as frames generated or removed.

10. The method of claim 1, wherein generating the frame, synchronizing the catalogue with the client, and a process to receive requests for frames from remote clients are each performed asynchronously with respect to each other.

11. A method of remotely accessing a cinematic production, comprising:
    receiving, at a remote client, a catalogue of frame descriptors from a server;
    storing, at the remote client, the catalogue of frame descriptors to synchronize the remote client with the server, wherein the catalogue of frame descriptors at the remote client is updated to reflect dynamic changes in the catalogue of frame descriptors at the server;

requesting a frame of the cinematic production from the server using at least one frame identifier from the catalogue of frame descriptors as a request;

receiving the frame from the server; and caching the frame in a cache.

12. The method of claim 11, wherein the catalogue is a duplicate of a catalogue maintained at the server.

13. The method of claim 11, further comprising:

providing a remote access program that executes on a processor of a client device requesting the frame, the remote access program being responsive to an input provided by a user interface program, wherein when the input is received by the remote access program, the remote access program produces the request for the frame.

14. The method of claim 13, wherein the request comprises one of a globally unique identifier (GUID) of the frame and a frame rate.

15. The method of claim 13, wherein each frame descriptor in the catalogue comprises the frame identifier and associated metadata.

16. The method of claim 11, further comprising maintaining the frame in the cache for retrieval in response to a subsequent request for the frame.

17. A non-transitory computer-readable medium having stored thereon computer-executable instructions that when executed by a computing device perform a method comprising:

receiving a request that initiates generating of frames of a cinematic production, the request including a frame descriptor maintained in a catalogue of frame descriptors maintained at a remote client and synchronized with a server, the catalogue of frame descriptors at the remote client being updated to reflect dynamic changes in a catalogue of frame descriptors maintained by the server;

generating the frames and placing them into a cache;

placing a descriptor of each of the frames into the catalogue of frame descriptors;

adding the frames to the cache as raw RGB images; and encoding the RGB images for communication to a remote client in accordance with the request.

18. The non-transitory computer-readable medium of claim 17, further including instructions that perform the method comprising:

receiving the descriptor as an identifier; and looking up the frame associated with the identifier.

19. The non-transitory computer-readable medium of claim 18, wherein the descriptor includes the identifier and associated metadata provided by an application that created the cinematic production.

20. The non-transitory computer-readable medium of claim 17, further including instructions that perform the method comprising synchronizing the catalogue with remote clients.

* * * * *